(12) United States Patent
Antos et al.

(10) Patent No.: US 10,470,708 B2
(45) Date of Patent: Nov. 12, 2019

(54) HEADPHONE

(71) Applicant: KOKOON TECHNOLOGY LIMITED, London (GB)

(72) Inventors: Timothy Antos, London (GB); Richard Hall, Cambridge (GB)

(73) Assignee: KOKOON TECHNOLOGY LIMITED, London (GB)

( * ) Notice: Subject to any disclaimer, the term of this patent is extended or adjusted under 35 U.S.C. 154(b) by 299 days.

(21) Appl. No.: 15/527,994

(22) PCT Filed: Nov. 19, 2015

(86) PCT No.: PCT/GB2015/053531
§ 371 (c)(1),
(2) Date: May 18, 2017

(87) PCT Pub. No.: WO2016/079525
PCT Pub. Date: May 26, 2016

(65) Prior Publication Data
US 2017/0325738 A1    Nov. 16, 2017

Related U.S. Application Data (60) Provisional application No. 62/149,731, filed on Apr. 20, 2015.

(30) Foreign Application Priority Data

Nov. 19, 2014 (GB) .................................. 1420565.2

(51) Int. Cl.
*A61B 5/00* (2006.01)
*H04R 1/10* (2006.01)
(Continued)

(52) U.S. Cl.
CPC .......... *A61B 5/6803* (2013.01); *A61B 5/0478* (2013.01); *A61B 5/4812* (2013.01);
(Continued)

(58) Field of Classification Search
CPC ...... H04R 1/10; H04R 1/1008; H04R 1/1041; H04R 1/1091; H04R 5/033; H04R 5/0335;
(Continued)

(56) References Cited

U.S. PATENT DOCUMENTS 4,399,334 A    8/1983 Kakiuchi et al.
4,727,599 A    2/1988 Rappaport et al.
(Continued)

FOREIGN PATENT DOCUMENTS

CN    2070171 U    1/1991
EP    2 600 635 A1    6/2013
(Continued)

OTHER PUBLICATIONS

PCT/GB2015/053531, International Search Report and Written Opinion, dated Apr. 25, 2016.
(Continued)

*Primary Examiner* — Jason R Kurr
(74) *Attorney, Agent, or Firm* — Fay Sharpe LLP (57) ABSTRACT

A headphone (3, 4) comprises a body (5) forming a chamber (26) for enclosing an ear of a user of the headphone (3, 4). The body (5) has an acoustic seal (7) of a flexible material surrounding the chamber (26), and the body (5) has a cushion (8) extending around the acoustic seal (7) and separate from the acoustic seal (7). The cushion (8) has a first side face (38) for engaging with the head of the user.

11 Claims, 7 Drawing Sheets

(51) Int. Cl.
*A61B 5/0478* (2006.01)
*H04R 5/033* (2006.01)

(52) U.S. Cl.
CPC ......... H04R 1/1008 (2013.01); H04R 1/1041 (2013.01); H04R 1/1091 (2013.01); *A61B 5/4815* (2013.01); *H04R 5/033* (2013.01); *H04R 5/0335* (2013.01); *H04R 2201/10* (2013.01)

(58) Field of Classification Search
CPC ............ H04R 2460/00; H04R 2460/09; H04R 2460/11; H04R 2460/15; A61B 5/6803; A61B 5/0478; A61B 5/4812; A61B 5/4815; A61F 11/14
USPC .......................................................... 381/74
See application file for complete search history.

(56) References Cited

U.S. PATENT DOCUMENTS

| | | | |
|---|---|---|---|
| 4,856,118 A * | 8/1989 | Sapiejewski | A61F 11/14 2/209 |
| 4,958,697 A | 9/1990 | Moody | |
| 4,967,038 A | 10/1990 | Gevins et al. | |
| 4,989,271 A * | 2/1991 | Sapiejewski | A61F 11/14 2/209 |
| 5,740,812 A | 4/1998 | Cowan | |
| 6,154,669 A | 11/2000 | Hunter et al. | |
| 2003/0235313 A1 | 12/2003 | Kurzweil et al. | |
| 2005/0089185 A1* | 4/2005 | Allen | H04R 1/1008 381/370 |
| 2005/0105755 A1 | 5/2005 | Yueh | |
| 2007/0249952 A1 | 10/2007 | Rubin et al. | |
| 2008/0128198 A1 | 6/2008 | Du et al. | |
| 2009/0214060 A1* | 8/2009 | Chuang | A61B 5/0478 381/151 |
| 2010/0158301 A1* | 6/2010 | Kuhtz | H04R 1/1008 381/374 |
| 2012/0078820 A1 | 3/2012 | Azam | |
| 2012/0172744 A1 | 7/2012 | Kato et al. | |
| 2013/0329933 A1* | 12/2013 | Kolton | H04R 1/1008 381/371 |
| 2014/0076318 A1 | 3/2014 | Flower et al. | |
| 2014/0140567 A1 | 5/2014 | LeBoeuf et al. | |
| 2017/0339484 A1* | 11/2017 | Kim | A61B 5/0478 |

FOREIGN PATENT DOCUMENTS

| | | |
|---|---|---|
| EP | 2 804 395 A1 | 11/2014 |
| GB | 2 396 421 A | 6/2004 |
| GB | 2 447 640 B | 3/2012 |
| JP | 6-78386 A | 3/1994 |
| JP | 2001-187034 | 7/2001 |
| JP | 2011-13009 A | 6/2011 |
| KR | 10-2013-0005802 A | 1/2013 |
| KR | 10-2013-0064558 A | 6/2013 |
| KR | 2014-0082380 A | 7/2014 |
| WO | WO 2002/013676 A2 | 2/2002 |
| WO | WO 2006/041648 A2 | 4/2006 |
| WO | WO 2009/019517 A2 | 2/2009 |
| WO | WO 2011/055291 A1 | 5/2011 |
| WO | WO 2013/026481 A1 | 2/2013 |
| WO | WO 2014/074013 A1 | 5/2013 |

OTHER PUBLICATIONS

GB 1420565.2, Search Report Under Section 17, dated Mar. 9, 2015.
GB 142565.2, Further Search Report Under Section 17, dated Jul. 20, 2015.
Bell, "Best over-ear and on-ear headphones of 2014", *The Inquirer*, Feb. 14, 2014, http://www.theinquirer.net/inquirer/review/2327664/best-on-the-ear-and-over-ear-headphones-of-2014 p. 4—(Philips Action Fit and Pioneer Bass Head—picture & text).
MacManus, Sony to Offer New Stylish PC Headsets, *Sony Insider*, Mar. 1, 2010, pp. 1-10, http://www.sonyinsider.com/1020/03/01/sony-to-offer-new-stylish-pc-headsets.

* cited by examiner

HEADPHONE

The present invention relates to a headphone and more particularly to a headset having a pair of headphones.

Reference to an ear in the specification means the outer ear which is the external part of the ear (i.e. that which is beyond the side of the head).

A conventional full size or circumaural or standard over-ear headphone or ear-cup has an ear cushion of foam around its speaker or transducer so that a chamber is formed for enclosing an ear of a wearer of the headphone. The foam provides two distinct functions: audio isolation, and transferring mechanical pressure loading from the headphone.

When a person is using a headphone over a long period, the headphone can become uncomfortable due to the retention of heat where the user's head is in contact with the ear cushion.

Furthermore, a conventional headphone has a shape that often extends outwardly a significant distance perpendicular to the surface engaging the user's head. If a user is in bed and is wearing a headset having a pair of such headphones, this causes a significant obstruction/restriction to movement of the head. As the user moves in bed the headphones can be dislodged into an unintended position making them uncomfortable. This may also compromise the audio performance of the headphones. If a person rolls onto one of the headphones whilst in bed, the foam is significantly compressed increasing pressure in the ear chamber making the headphone uncomfortable to wear. The significant pressure may be applied in a non-uniform fashion which also makes the headphone uncomfortable to wear. Furthermore, this pressure may also be applied to a sensitive region behind and below the ear.

A user may wear the headset in bed to listen to audio (e.g. music, audio book) to relax the mind or simply for entertainment. However, if a user falls asleep the audio may continue which may disturb the user's sleep later.

It is an object of the present invention to provide a headphone to alleviate at least one of the above-mentioned problems.

According to one aspect of the present invention there is provided a headphone comprising a body forming a chamber for enclosing an ear of a user of the headphone, the body having an acoustic seal made of a flexible material surrounding the chamber, the body having at least one cushion extending around the acoustic seal and separate from the acoustic seal, the at least one cushion having a first side face for engaging with the head of the user.

The at least one cushion can be made from a flexible material which is the same or different from the flexible material of the acoustic seal.

By having a headphone with an acoustic seal made of a flexible material, and at least one cushion separate from the acoustic seal, this gives more freedom in selecting materials which may be more particularly suited for the function of audio isolation, or the function of transferring mechanical pressure loading from the headphone. The acoustic seal requires a smaller area of contact with the skin of a user of the headphone than a conventional headphone. The acoustic seal can be very soft and flexible as it does not need to support the mechanical load. The at least one cushion, as it has no audio barrier requirements, can be made to provide much more comfort than a conventional headphone.

The headphone may be made of predominantly flexible materials, such as rubber/silicon, allowing the body of the headphone to mould to the shape of the head. As the body moulds to the shape of the head it enables pressure to spread consistently over the maximum area thus increasing comfort.

The flexible material of the acoustic seal may be expandable so that the acoustic seal is arranged to expand towards the at least one cushion extending around the acoustic seal when the headphone is pressed against the head of the user.

The headphone may include a channel separating the acoustic seal from the at least one cushion extending around the acoustic seal. The acoustic seal may be arranged to expand into the channel when the headphone is pressed against the head of the user.

The body may have one continuous cushion extending around the acoustic seal. Alternatively, the body may have a plurality of cushions extending around the acoustic seal with or without a gap between adjacent cushions.

The body of the headphone may have a second side face opposite the first side face. Venting means may be provided between the first side face and the second side face. The venting means may comprise a plurality of openings in the first side face, a plurality of openings in the second side face, and a cavity which connects the first side face openings to the second side face openings.

A plurality of flexible supports may extend through the cavity between first and second side faces.

The venting means may comprise a plurality of conduits, each said conduit extending between the first and second side faces.

The venting means are for circulating and venting air, and heat is able to dissipate easily via the venting means. The venting means are in the at least one cushion, and since the at least one cushion has no audio barrier requirements, this makes the at least one cushion extremely breathable. This ensures that the headphone remains cool and comfortable, particularly if a headset including the headphone is, say, worn through the night.

A headset may be provided which comprises a headband, and at least one headphone wherein the or each headphone is as described above. The at least one headphone is connected to the headband and comprises a speaker, and said headband includes at least one of a power source and a main circuit board for the at least one headphone. By accommodating the power source and/or the main circuit board in the headband, the size of the headphone can be reduced to provide the lowest or shallowest headphone profile possible relative to the head without making contact with the ear of the user.

The second side face of the headphone body may join the first side face and form an acute angle with the first side face at said joining of not more than approximately 45° at least at, or in the vicinity of, the lowermost part of the headphone. In the vicinity of the lowermost part of the headphone may be the part of the headphone extending around the part of a periphery of the chamber corresponding to the lobe part of the ear of a user of the headphone. The periphery of the chamber may have a substantially straight portion for positioning in front of the ear and a substantially curved portion substantially conforming to the shape of the helix and lobe parts of the ear, the two portions joining at first upper and lower points of the periphery. There may be another point on the substantially curved portion of the periphery where a rear part of the curved portion joins a lower part of the curved portion (i.e. the lower part is curved more to the lowermost part of the periphery whereas the rear part is curved more to the part of the periphery to be to the rear of the ear). In the vicinity of the lowermost part of the headphone may be the part of the headphone extending around the chamber between approximately the first lower point and said another point. The second side face may form an acute angle with the first side face at said joining of not more than approximately 45° in the vicinity of the part of the headphone intended to be positioned adjacent the rear of an ear of a user of the headphone. The chamber periphery may have a second upper point where an upper part of the curved portion joins a rear part of the curved portion (i.e. the upper part is curved more to the uppermost part of the periphery whereas the rear part is curved more to the part of the periphery to be to the rear of the ear). In the vicinity of the part of the headphone intended to be positioned adjacent the rear of the ear may be the part of the headphone extending around the chamber between approximately the second upper point and said another point. The second side face may form an acute angle with the first side face at said joining of not more than approximately 45° in the vicinity of the part of the headphone intended to be positioned in front of an ear of a user of the headphone. In the vicinity of the part of the headphone intended to be positioned in front of the ear may be the part of the headphone extending around the chamber between approximately the first upper and lower points. By the second side face joining the first side face at an acute angle of not more than approximately 45°, this also helps provide the lowest or shallowest headphone profile possible relative to the user's head.

By the headphone having the lowest or shallowest profile possible relative to the head of the user, this provides effectively unrestricted movement of the user's head when the user is lying down as the headphone would provide a minimal obstruction. Also, by the headphone having a lower profile than a conventional full size headphone it would not sink so much into a surface of say a pillow when the user leans or rolls onto the headphone. As a result the pillow would be less deformed and would provide better support for the user's head. The user's head can roll easily and comfortably onto its side without dislodging the headphones or uncomfortably focusing pressure in one region. This ensures that the headphone remains secure on the user when the user is say asleep on a bed and that the headphone fits snugly.

The main circuit board of the headband of the headset may comprise a plurality of circuit boards electrically connected to each other. The circuit boards may be connected to each other in series.

The headset may include at least one electroencephalography (EEG) sensor mounted in or on an underside of the headband, the underside arranged to face the scalp of a user of the headphone. An EEG sensor is a known sensor used in reading brain activity of a user such as when the user is asleep. The at least one EEG sensor may be used to monitor when a user using the headset falls asleep so that any audio being played can be automatically stopped.

The headphone described above may include at least one EEG sensor mounted in the first side face.

At least part of the second side face may be covered by a flexible porous material.

The periphery of the chamber may have a substantially straight portion for positioning in front of the ear and a substantially curved portion substantially conforming to the shape of the helix and lobe parts of the ear, the two portions joining at first upper and lower points of the periphery, the first side face having a radial width which extends from adjacent the chamber periphery to the periphery of the first side face, the radial width having a maximum value in the vicinity of the first upper point. The location of the maximum value of the radial width would be in front of the ear of a user of the headphone and would be in a region of the head of the user forward of their jawline wherein this region is less sensitive and more tolerant of pressure, whereas the region behind the ear is significantly more sensitive.

The radial width may have the maximum value at a point between the first upper point and the first lower point. The maximum value may be closer to the first upper point than to the first lower point. The radial width may have a minimum value in the lower part or in the vicinity of the lowest point of the curved portion.

The chamber periphery may have a second lower point at the lowest part of the curved portion, and a second upper point where an upper part of the curved portion joins a rear part of the curved portion, the surface area of one section of the first side face extending around the acoustic seal between approximately the second lower point and the second upper point being larger than the surface area of the remaining section of the first side face, said remaining section being adjacent the rear of the ear when the headphone is being worn. The surface area of said one section of the first side face is in front of a line or an imaginary line between the second lower and upper points, the said one section being adjacent the front of the ear when the headphone is being worn. The imaginary line approximately corresponds to the jawline of a user of the headphone. The imaginary line may be at a distance in front of the jawline which may be slight. When a user is, say, in bed or reclining in a seat or lying on a couch, the user's head may lean on the headphone. The pressure of the user's head is spread across the first side face of the at least one cushion of the headphone and, by the surface area of the one section being greater than the remaining section, the majority of the pressure is loaded onto the less sensitive region of the head forward of the jawline providing more comfort. The surface area of said one section of the first side face may be at least 1.4 times larger than the surface area of the remaining section of the first side face.

According to another aspect of the present invention there is provided a headphone comprising a body forming a chamber for enclosing an ear of a user of the headphone, the body having a first side face for engaging with the head of the user, a second side face opposite the first side face, and venting means between the first side face and the second side face.

According to another further aspect of the present invention there is provided a headset comprising a headband, and at least one headphone connected to the headband, said at least one headphone comprising a speaker, and said headband including at least one of a power source and a main circuit board for the at least one headphone.

According to yet another further aspect of the present invention there is provided a headphone comprising a body forming a chamber for enclosing an ear of a user of the headphone, the body having a first side face for engaging with the head of the user, and a second side face opposite the first side face, wherein the second side face joins the first side face and forms an acute angle with the first side face at said joining of not more than approximately 45° at least at, or in the vicinity of, the lowermost part of the headphone.

According to still yet another further aspect of the present invention there is provided a headphone comprising a body forming a chamber for enclosing an ear of a user of the headphone, the periphery of the chamber having a substantially straight portion for positioning in front of the ear and a substantially curved portion substantially conforming to the shape of the helix and lobe parts of the ear, the two portions joining at first upper and lower points of the periphery, the body having a first side face for engaging with the head of the user, the first side face having a radial width which extends from adjacent the chamber periphery to the periphery of the first side face, the radial width having a maximum value in the vicinity of the first upper point.

Embodiments of the present invention will now be described, by way of example, with reference to the accompanying schematic drawings, in which.

Referring to FIGS. 1 to 4 of the accompanying drawings, a headset 1 comprises a headband 2 connecting a pair of headphones 3, 4 together.

Referring to FIGS. 5 to 9, each headphone 3, 4 comprises a body 5 having a central body portion 6, an acoustic or audio seal 7 surrounding a chamber 26, a cushion 8 surrounding the acoustic seal 7 and separate from the acoustic seal 7, and an outer shell 9 having a convex outer surface 10 and a concave inner surface 11.

Figure 1:
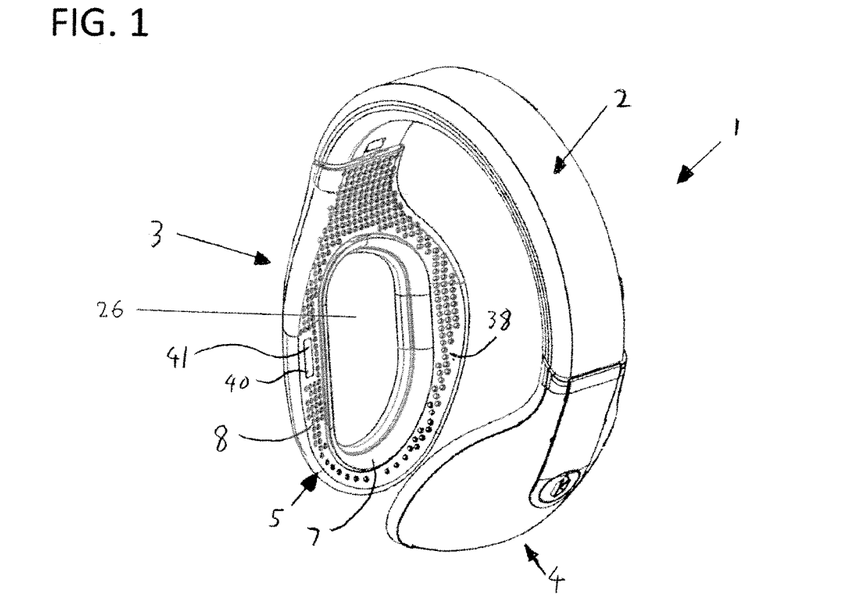
FIG. 1 is a perspective view of a headset comprising a pair of headphones wherein each headphone is in accordance with a first embodiment of the present invention.
Figure 2:
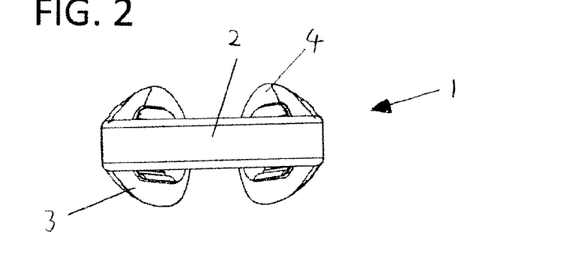
FIGS. 2 to 4 are top, front and side views, respectively, of the headset.
Figure 3:
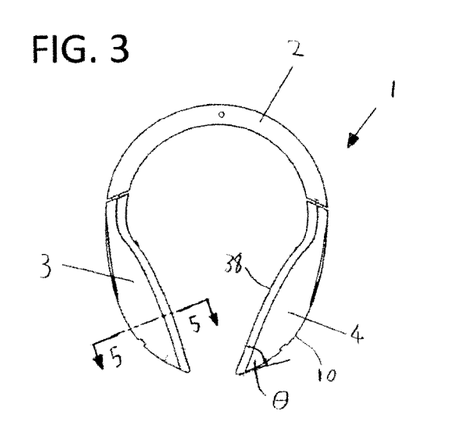
Figure 4:
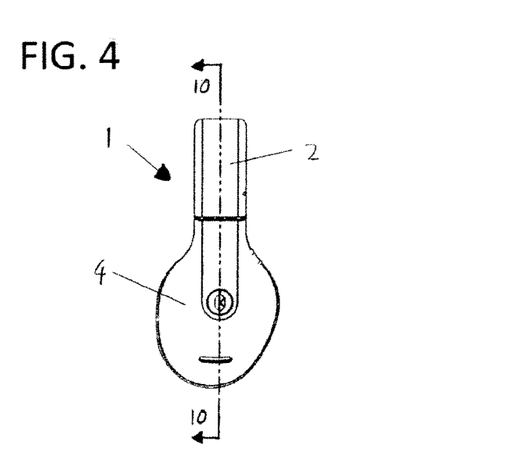
Figure 5:
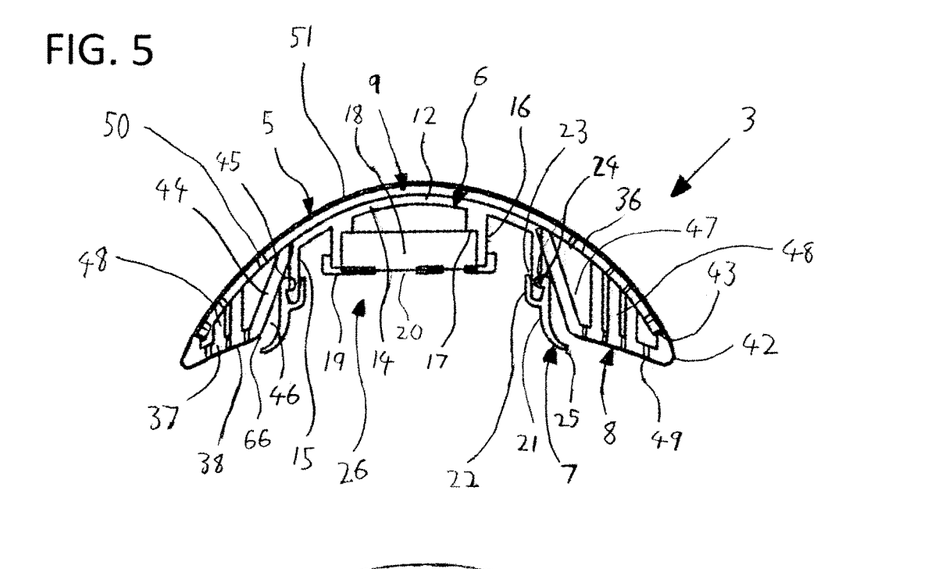
FIG. 5 is a sectional view of a headphone of the headset taken along lines 5-5 of FIG. 3.
Figure 6:
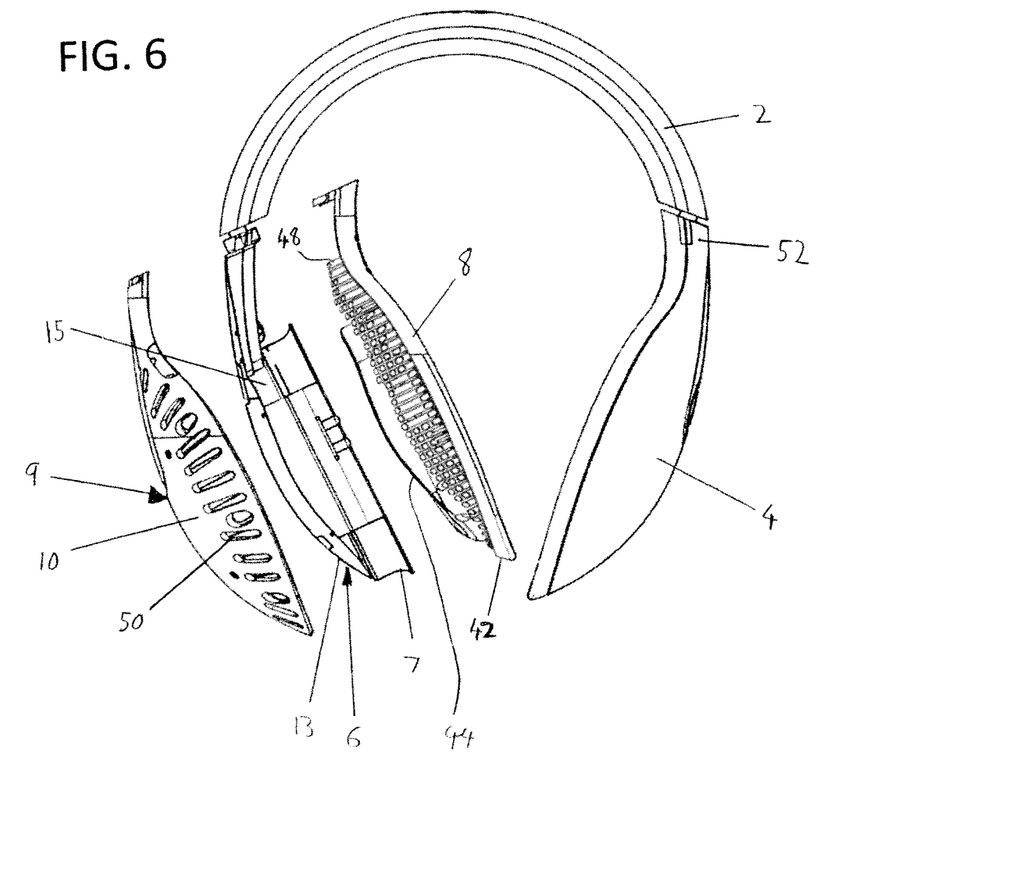
FIG. 6 is a front view of the headset showing an exploded view of one of the headphones.
Figure 7:
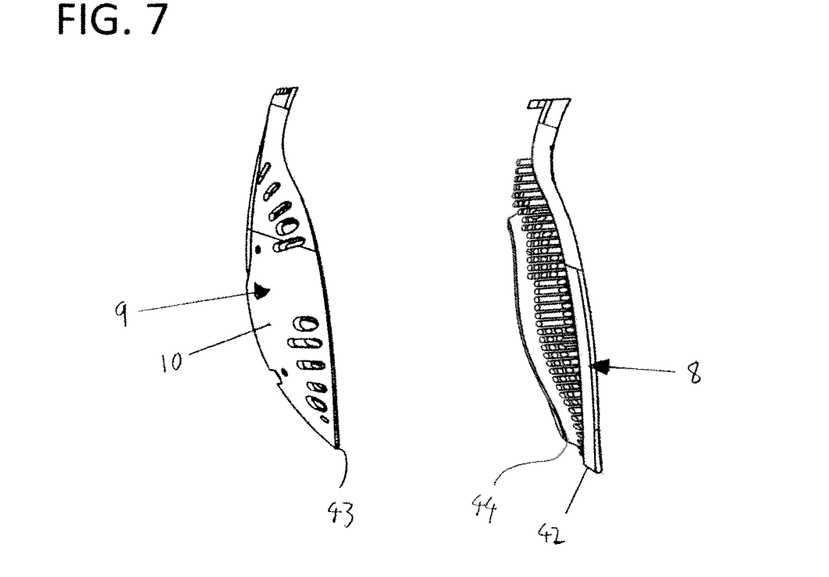
FIGS. 7 and 8 are exploded side and perspective views, respectively, of an outer shell and cushion of the headphone of FIG. 6.
Figure 8:
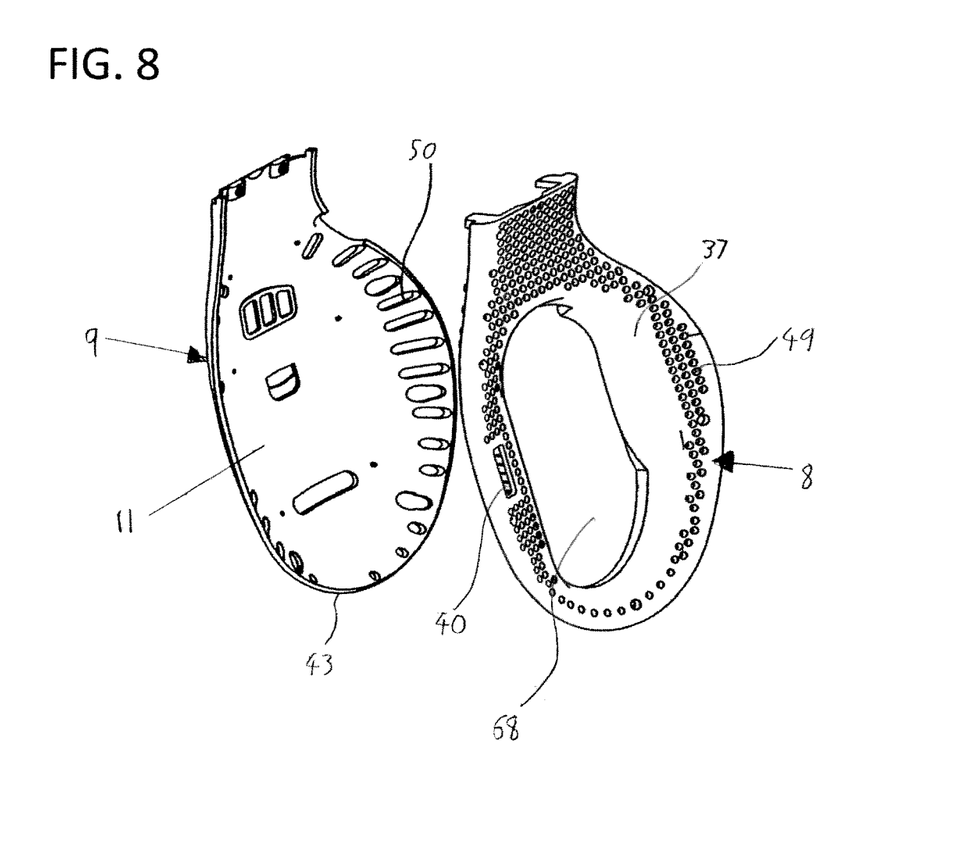

The central body portion 6 has a base 12 with a convex outer surface 13 and a concave inner surface 14. The central body portion 6 is fixed to the outer shell 9 so that base convex outer surface 13 of the central body portion 6 is against the shell concave inner surface 11. A continuous outer wall 15 extends from a perimeter of the base concave inner surface 14, and an inner wall 16 extends from the base 12 and is surrounded by the outer wall 15. The inner wall 16 has an inner step 17 towards the end of the wall 16 distal from the base 12. A transducer assembly 18 is mounted on the step 17 and is surrounded by the inner wall 16. A cap 19 is fixed over the distal end of the wall 16 to hold the transducer assembly 18 within the inner wall 16 of the central body portion 6, and the cap 19 has apertures 20.

The acoustic seal 7 is made of a first flexible expandable material such as silicon. The acoustic seal 7 has a continuous main wall portion 21 surrounding the chamber 26 and an inner wall portion 22 extending in from the main wall portion 21 at a base of the main wall portion 21 so as to form a groove 23 into which a distal end of the central body portion outer wall 15 is received. The acoustic seal main wall portion 21 has a flange 24 extending into the groove 23 so that the central body portion outer wall 15 is held in the groove 23 by an interference grip between the flange 24 and the acoustic seal inner wall portion 22. The end 25 of the acoustic seal main wall portion 21 distal from the base of the seal 7 tapers and bends or flares outwardly.

The central body portion 6 and the acoustic seal 7 extending from the central body portion outer wall 15 form the chamber 26 for enclosing an ear 70 (see FIG. 13) of a user of the headphone 3, 4, wherein the distal end 25 of the acoustic seal 7 defines the periphery of the chamber 26. The chamber periphery 25 has a substantially straight portion 28 for positioning in front of the ear and a substantially curved portion 29 substantially conforming to the shape of the helix and lobe parts of the ear. The two portions 28, 29 join at first upper and lower points 30, 31 of the periphery 25. The chamber periphery 25 has a second lower point 32 at the lowest part of the curved portion 29, and a second upper point 33 where an upper part 34 of the curved portion 29 joins a rear part 35 of the curved portion 29. The chamber periphery 25 has another or a third point 69 where the rear part 35 of the curved portion 29 joins a lower part 72 of the curved portion 29.

Figure 9:
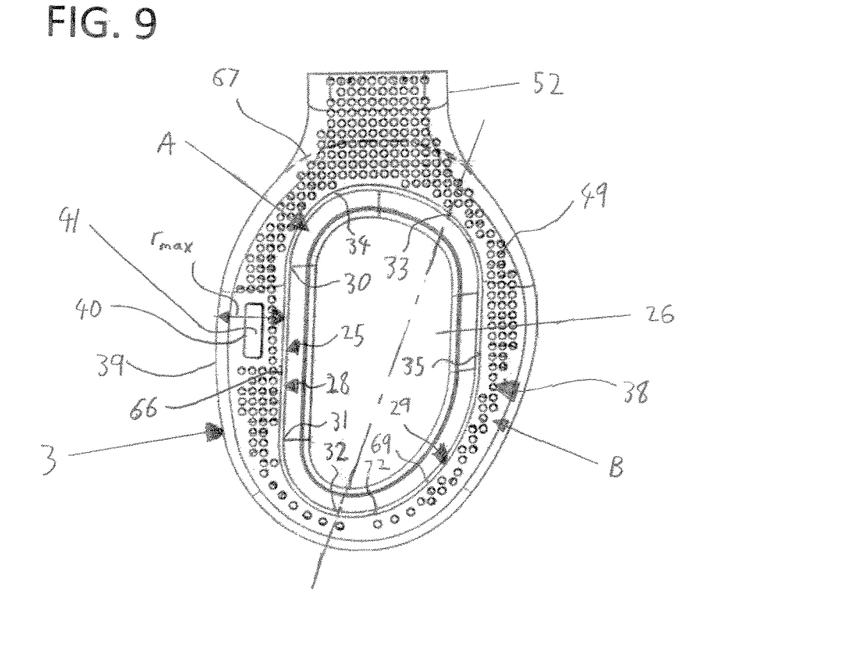
FIG. 9 is a view of an inner side face of the headphone of FIG. 6.

The cushion 8 is made of a material such as rubber or silicon. The cushion 8 surrounds the central body portion outer wall 15 and the acoustic seal 7 and is against the portion 36 of the concave inner surface 14 of the outer shell 9 which extends beyond the central body portion 6. The cushion 8 has a base portion 37 with a central opening or aperture 68, and a bottom face of the base portion 37 comprises a first side face 38 for engaging the head of the user of the headphone 3, 4. The first side face 38 has a radial width which extends from an inner edge 66 of the base portion 37 surrounding the opening 68 and adjacent the chamber periphery 25 to an outer edge or periphery 39 of the base portion 37. The radial width has a maximum value $r_{max}$ at a point between the first upper point 30 and the first lower point 31 wherein this point is closer to the first upper point 30.

The surface area of one section A of the first side face 38 extends around the acoustic seal 7 between approximately the second lower and upper points 32, 33 in front of the chamber 26. The one section A is larger than the surface area of the remaining section B of the first side face 38. The surface area of the one section A of the first side face 38 may be at least 1.4 times larger than the surface area of the remaining section B of the first side face 35.

The cushion base portion 37 has an aperture 40 in the portion of the first side face 38 to be in front of the ear of the user, and in this aperture 40 is mounted an electroencephalography (EEG) sensor 41.

The cushion base portion outer edge 39 has a rim 42 and the outer shell 9 is fitted within the rim 42 so that the perimeter edge 43 of the outer shell 9 engages the rim 42. An inner wall 44 extends from the cushion base portion inner edge 66 and surrounds the central body portion 6. The cushion inner wall is slanted inwardly from the base portion 37 so that its distal end engages the place where the central body portion outer wall 15 meets the outer shell 9. The cushion base portion inner wall 44 is adjacent the base 45 of the acoustic seal main wall portion 21, and a gap or channel 46 is formed between the rest of the acoustic seal main wall portion 21 and the cushion base portion inner wall 44. A cavity 47 is formed between the cushion base portion 37 and the outer shell 9 and is bounded by the cushion base portion rim 42 and the cushion base portion inner wall 44. The cushion 8 has a plurality of flexible tube supports 48 which extend from the cushion base portion 37 to the outer shell 9. There is a plurality of vent openings 49 extending through, and spread around, the cushion base portion 37.

The convex outer surface 10 of the outer shell 9 forms a second side face of the body 5 which is opposite the first side face 38. There is a plurality of vent openings 50 extending through, and spread around, the outer shell portion 36 which extends beyond the central body portion 6. The second side face 10 is covered by a porous flexible fabric 51.

The second side face 10 joins the first side face 38 and forms an acute angle θ (see FIG. 3) with the first side face 38 at the joining of not more than approximately 45° around the periphery of the headphone 3, 4 except for the portion of the headphone 3, 4 radial from the upper part 34 of the chamber periphery curved portion 29. Part of this headphone portion extends beyond the first side face 38 which engages the head of the user. This part is referred to as the top portion 52 of the headphone 3, 4 and the top portion 52 extends to the headband 2. The boundary between the top portion 52 and the first side face 38 is indicated by a dashed line 67 on FIG. 9. The top portion 52 is configured so that where it is adjacent the headband 2 it has the same sectional shape and size as the headband 2.

Figure 10:
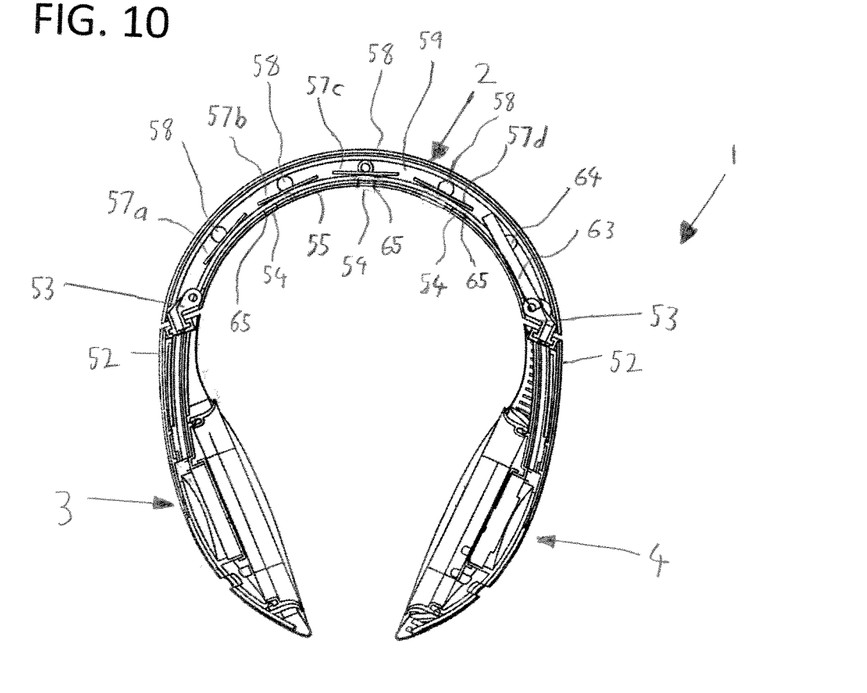
FIG. 10 is a sectional view of the headset taken along lines 10-10 of FIG. 4.
Figure 11:
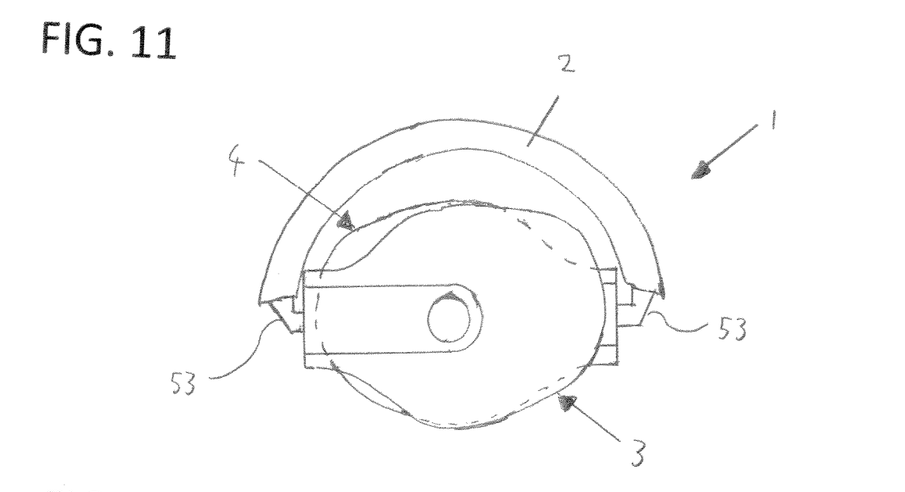
FIG. 11 is a perspective view of the headset in a stored position.
Figure 12:
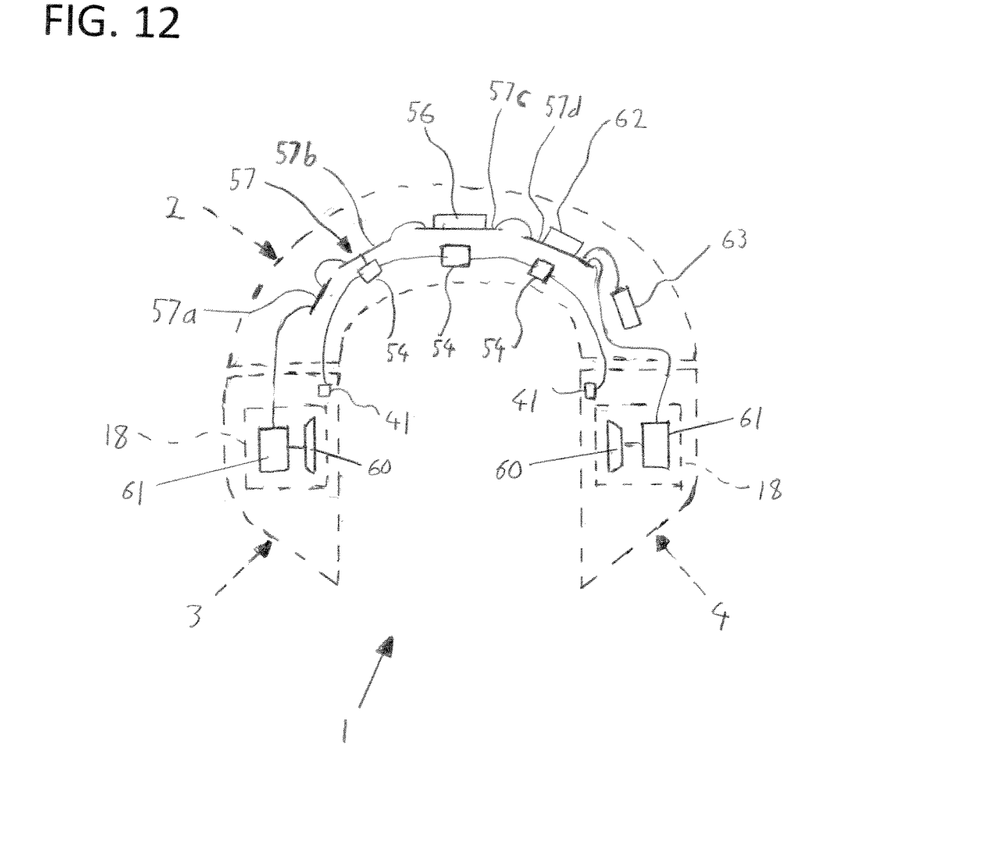
FIG. 12 is a block diagram of the headset.

Referring to FIGS. 10 to 12, the headband 2 extending between the top portion 52 of each headphone 3, 4 is connected by a hinged and rotatable connector 53 to each headphone 3, 4. This enables the headphones 3, 4 to be swung inwards and be rotated through 90° so that when the headset 1 is not in use it can be stored compactly (see FIG. 11).

The headband 2 is hollow and the underside 55 of the headband 2, which is arranged to face the scalp of a user of headset 1, has a plurality of apertures 65 spaced in series along the underside 55 and an EEG sensor 54 is mounted in each aperture 65. The EEG sensors 54 in the headband 2, together with the EEG sensor 41 in each headphone 3, 4, are connected to a central processor 56 mounted on a main circuit board 57 inside the headband 2. The main circuit board 57 comprises a plurality of circuit boards 57a, 57b, 57c, 57d electrically connected to each other in series so that the main circuit board 57 can fit inside the headband 2. Each circuit board 57a, 57b, 57c, 57d is mounted to a mounting 58 which connects the circuit board 57a, 57b, 57c, 57d to a side 59 of the headband 2, and the circuit boards 57a, 57b, 57c, 57d are above the EEG sensors 54.

The transducer assembly 18 in each headphone 3, 4 is connected to the central processor 56 in the headband 2 and each transducer assembly 18 comprises a speaker 60 and a driver 61.

A Bluetooth module 62 is mounted on the main circuit board 57 in the headband 2 and the Bluetooth module 62 can communicate with a portable electronic communication device such as a smart phone or a hand-held tablet PC.

Also inside the headband 2, there is a power source in the form of a battery 63 for providing power to the headset 1. The battery 63 is held by a mounting 64 to the side 59 of the headband 2

In use, the headset 1 is worn on the head of a user with each ear of the user being received in the chamber 26 of a respective headphone 3, 4, and the headband 2 being positioned over the scalp of the user.

Figure 13:
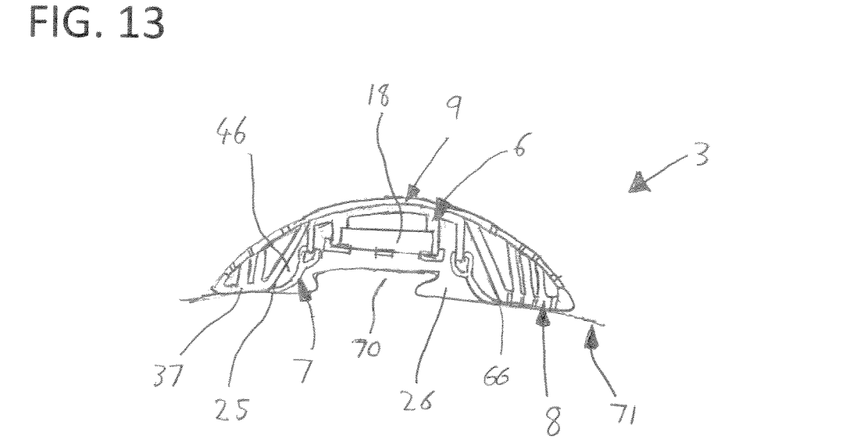
FIG. 13 is a sectional view similar to FIG. 5 with the headphone on the side of a head of a user of the headset.

As each headphone 3, 4 is placed against the head or skull 71 of the user, the body 5 moulds to the shape of the head (see FIG. 13). The loading of the headphone 3,4 causes the acoustic seal 7 to expand so that the tapered end 25 of the seal 7 engages the inner edge 66 of the cushion base portion 37 closing the opening to the gap 46 between the acoustic seal 7 and the cushion base portion 37.

The EEG sensors 54 in the headband 2 and the EEG sensor 41 in each headphone 3, 4 are arranged to measure EEG signals associated with brain activity in the head of the user. These signals are monitored by the central processor 56, and the central processor 56 is arranged to control the volume of sound from each speaker 60 via their respective speaker driver 61 in relation to these signals.

Signals from the EEG sensors 41, 54 received by the central processor 56 could be transmitted by the Bluetooth module 62 to a said portable electronic communication device, and the portable electronic communication device could be used to change or control the sound coming from the speakers 60 of the headphones 3, 4.

Figure 14:
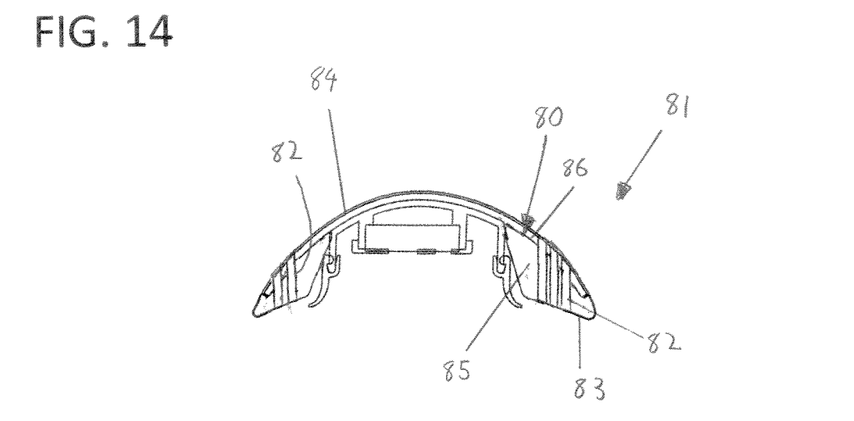
FIG. 14 is a sectional view of a modified headphone.

In a modification as illustrated in FIG. 14, the body 80 of each headphone 81 has a plurality of conduits 82 extending between the first and second side faces 83, 84 to provide venting, the conduits 82 extending through the cushion 85 and the outer shell 86 of the body 80.

Figure 15:
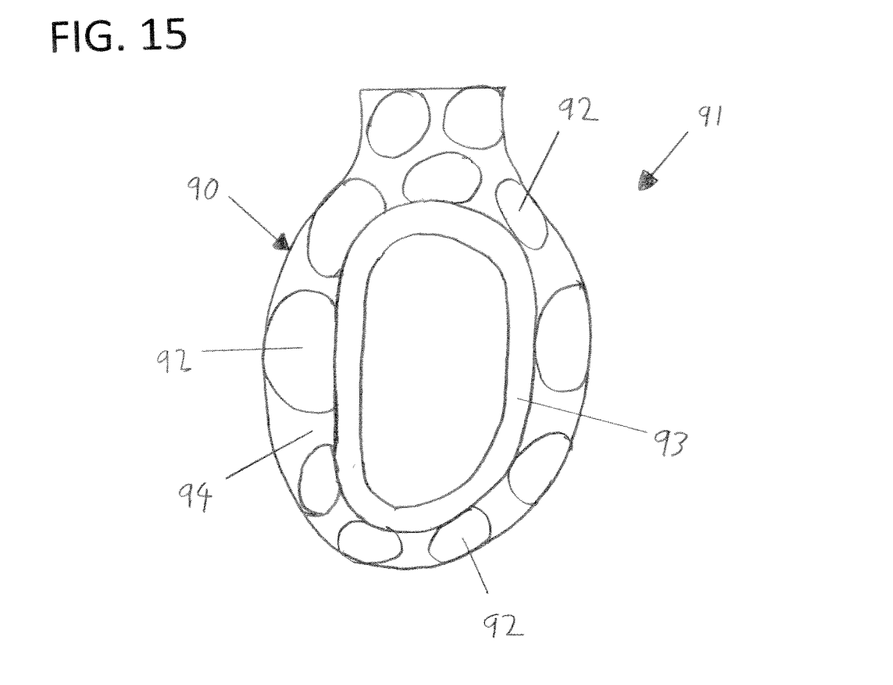
FIG. 15 is a view of an inner side face of another modified headphone.

In another modification as illustrated in FIG. 15, the body 90 of each headphone 91 has a plurality of cushions 92 spaced around the acoustic seal 93 with there being gaps 94 between the cushions 92.

Whilst particular embodiments have been described, it will be understood that various modifications may be made without departing from the scope of the claimed invention.

The invention claimed is:

1. A headphone comprising a body forming a chamber for enclosing an associated ear of an associated user of the headphone, the body having an acoustic seal made of a flexible material surrounding the chamber, the body having at least one cushion extending around the acoustic seal and separate from the acoustic seal, the at least one cushion having a first side face for engaging with an associated head of the associated user, wherein the body has a second side face opposite the first side face, and at least one vent including a plurality of openings in the first side face, a plurality of openings in the second side face, and a cavity which connects the first side face openings to the second side face openings, the at least one vent being in the at least one cushion.

2. The headphone as claimed in claim 1, wherein the flexible material of the acoustic seal is expandable so that the acoustic seal is arranged to expand towards the at least one cushion when the headphone is pressed against the associated head of the associated user.

3. The headphone as claimed in claim 1, wherein a plurality of flexible supports extends through the cavity between the first and second side faces.

4. The headphone as claimed in claim 1, wherein at least part of the second side face is covered by a flexible porous material.

5. The headphone as claimed in claim 1, including at least one electroencephalography (EEG) sensor mounted in the first side face.

6. A headset comprising a headband, and at least one headphone as claimed in claim 1, wherein said at least one headphone is connected to the headband and comprises a speaker, and said headband includes at least one of a power source and a main circuit board for the at least one headphone.

7. The headset as claimed in claim 6, wherein the headband includes both the power source and the main circuit board.

8. The headset as claimed in claim 6, wherein the main circuit board comprises a plurality of circuit boards electrically connected to each other.

9. The headset as claimed in claim 8, wherein the circuit boards are connected to each other in series.

10. The headset as claimed in claim 6, including at least one electroencephalography (EEG) sensor mounted in or on an underside of the headband, the underside arranged to face an associated scalp of an associated user of the headphone.

11. A headphone comprising a body forming a chamber for enclosing an associated ear of an associated user of the headphone, the body having an acoustic seal made of a flexible material surrounding the chamber, the body having at least one cushion extending around the acoustic seal and separate from the acoustic seal, the at least one cushion having a first side face for engaging with an associated head of the associated user, wherein the body has a second side face opposite the first side face, and at least one vent including a plurality of openings in the first side face, a plurality of openings in the second side face, wherein the at least one vent comprises a plurality of conduits, each said conduit extending between the first and second side faces.

* * * * *